(12) United States Patent
Scharioth et al.

(10) Patent No.: US 12,036,111 B2
(45) Date of Patent: Jul. 16, 2024

(54) METHOD OF IMPLANTATION OF AN INTRAOCULAR LENS IN A CILIARY SULCUS OF AN EYE

(71) Applicant: MEDICONTUR HOLDING LTD., Zsambek (HU)

(72) Inventors: Gabor B. Scharioth, Recklinghausen (DE); Laszlo F. Kontur, Munich (DE); Rudiger Dworschak, Deidesheim (DE)

(73) Assignee: MEDICONTUR HOLDING LTD., Zsámbék (HU)

( * ) Notice: Subject to any disclaimer, the term of this patent is extended or adjusted under 35 U.S.C. 154(b) by 816 days.

(21) Appl. No.: 17/109,841

(22) Filed: Dec. 2, 2020

(65) Prior Publication Data

US 2021/0085449 A1    Mar. 25, 2021

Related U.S. Application Data

(63) Continuation-in-part of application No. 16/190,906, filed on Nov. 14, 2018, now abandoned, which is a
(Continued)

(30) Foreign Application Priority Data

Sep. 14, 2011 (FR) ...................... 1158196

(51) Int. Cl.
*A61F 2/16* (2006.01)
(52) U.S. Cl.
CPC .......... *A61F 2/1645* (2015.04); *A61F 2/1602* (2013.01); *A61F 2002/16902* (2015.04); *A61F 2002/169053* (2015.04)
(58) Field of Classification Search
None
See application file for complete search history.

(56) References Cited

U.S. PATENT DOCUMENTS

| 4,819,617 A | * | 4/1989 | Goldberg ............. A61K 9/0048 |
| | | | 623/4.1 |
| 5,693,094 A | * | 12/1997 | Young ...................... A61F 2/16 |
| | | | 128/898 |

(Continued)

FOREIGN PATENT DOCUMENTS

| EP | 1475055 A1 | 4/2010 |
| EP | 2319457 A1 | 5/2011 |

(Continued)

*Primary Examiner* — Leslie A Lopez
(74) *Attorney, Agent, or Firm* — Olson & Cepuritis, Ltd.

(57) ABSTRACT

A method for the correction of the near vision of a patient suffering from age-related macular degeneration (AMD) and having a pseudophakic eye having at least one primary intraocular lens (IOL) implanted in a capsular bag in a posterior chamber of the eye, comprising:

implanting a secondary IOL, made from a foldable soft material, between an iris of the eye and the primary IOL, wherein the secondary IOL comprises an optically active lens part having an optical axis and a plurality of evenly spaced haptics around the optically active lens part, the optically active lens part having a central optical lens portion and a peripheral optical lens portion surrounding the central optical lens portion, the central optical lens portion being a positive lens and having a refractive power that differs from a refractive power of the peripheral optical lens portion by +5 diopters up to +25 diopters, placing the central optical lens portion of the secondary IOL in an aligned position optically coaxial to the at least one primary IOL for magnifying and focusing an image projected by the central lens portion through the at least one primary IOL on a fovea of a retina of the eye, and (Continued)

fixing the secondary IOL in the aligned position by arranging the plurality of haptics behind the iris in a ciliary sulcus of the eye.

25 Claims, 9 Drawing Sheets

Related U.S. Application Data continuation-in-part of application No. 15/304,860, filed as application No. PCT/HU2014/000032 on Apr. 18, 2014, now abandoned, said application No. 16/190,906 is a continuation-in-part of application No. 13/609,339, filed on Sep. 11, 2012, now abandoned.

(56) References Cited

U.S. PATENT DOCUMENTS

| | | | |
|---|---|---|---|
| 6,197,057 B1 * | 3/2001 | Peyman | A61F 2/1651 623/6.34 |
| 6,461,384 B1 * | 10/2002 | Hoffmann | A61F 2/1616 623/6.37 |
| 2005/0027355 A1 | 2/2005 | Murakami et al. | |
| 2005/0288784 A1 | 12/2005 | Peyman | |
| 2006/0142855 A1 * | 6/2006 | Vaudant | B29D 11/023 623/6.49 |
| 2006/0206206 A1 * | 9/2006 | Peyman | A61F 2/1648 623/6.34 |
| 2006/0259138 A1 | 11/2006 | Peyman | |
| 2007/0270947 A1 | 11/2007 | Peyman | |
| 2012/0136438 A1 * | 5/2012 | Moriarty | A61F 2/1602 623/6.43 |

FOREIGN PATENT DOCUMENTS

| | | | | |
|---|---|---|---|---|
| WO | 1987007496 A1 | | 12/1987 | |
| WO | 1989009576 A1 | | 10/1989 | |
| WO | 2001032105 A1 | | 5/2001 | |
| WO | 2005039451 A1 | | 5/2005 | |
| WO | 1020070026672 | * | 8/2007 | B29D 11/02 |
| WO | 2010131955 A1 | | 11/2010 | |
| WO | 2010136798 A1 | | 12/2010 | |

* cited by examiner

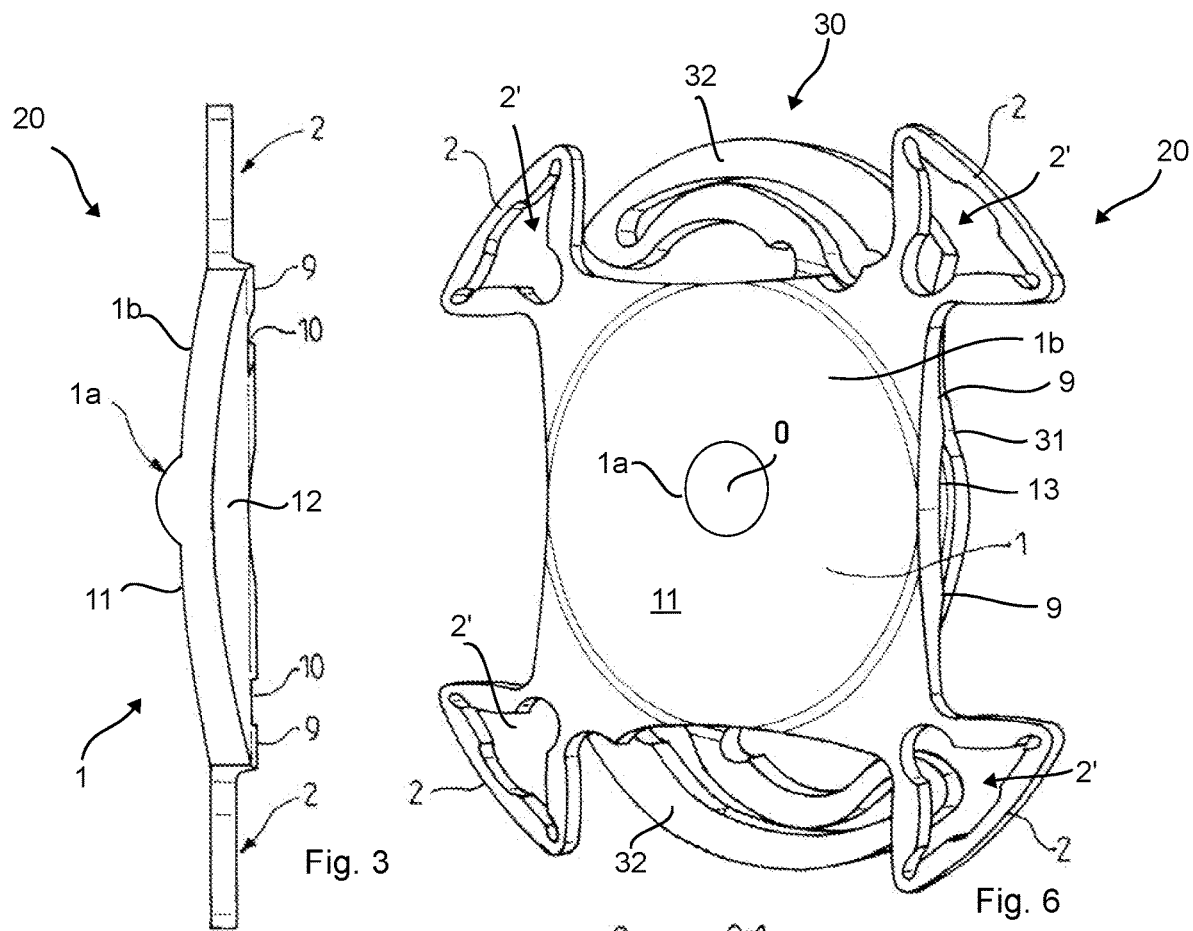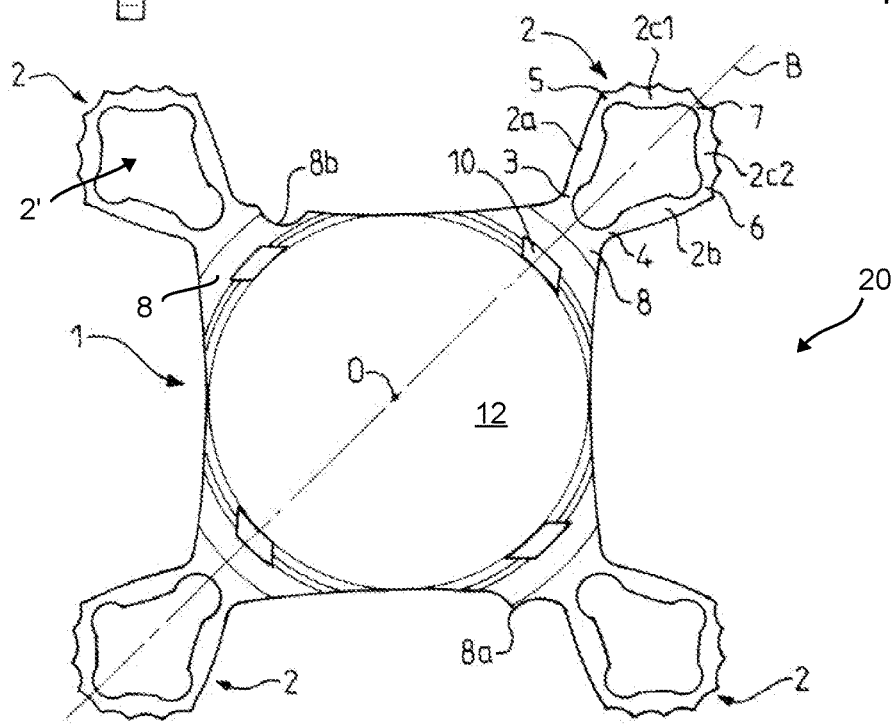

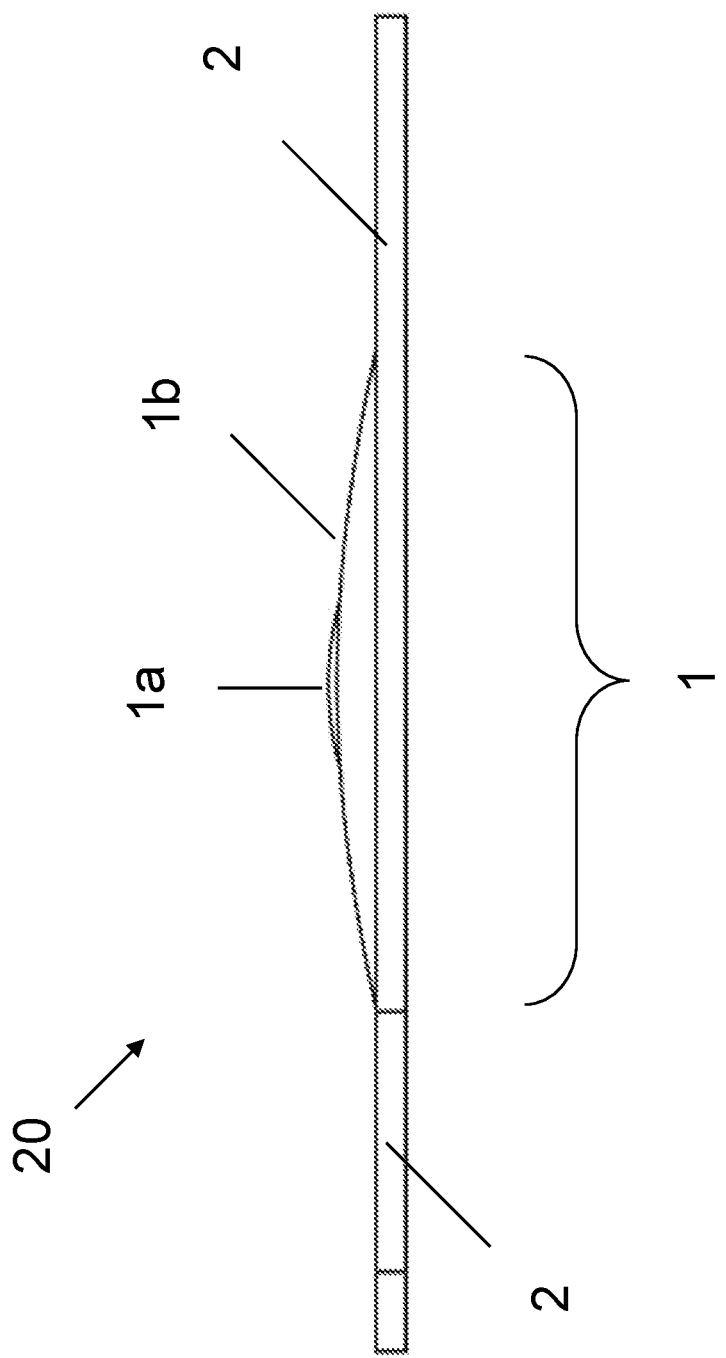

METHOD OF IMPLANTATION OF AN INTRAOCULAR LENS IN A CILIARY SULCUS OF AN EYE

CROSS-REFERENCE TO RELATED APPLICATIONS

This application is a continuation-in-part of U.S. Ser. No. 16/190,906, filed on Nov. 14, 2018, which is a continuation-in-part of U.S. Ser. No. 15/304,860, filed on Oct. 18, 2016, now abandoned, which is a U.S. National Phase application under 35 U.S.C. 371 of PCT/HU2014/000032, filed on Apr. 18, 2014; and U.S. Ser. No. 16/190,906 is a continuation-in-part of U.S. Ser. No. 13/609,339, filed on Sep. 11, 2012, now abandoned; each of which is incorporated herein by reference in its entirety.

TECHNICAL FIELD

The present invention relates to a method for the correction of the near vision of a patient suffering from age-related macular degeneration (AMD) and having a pseudophakic eye having at least one primary intraocular lens (IOL) implanted in a capsular bag in a posterior chamber of the eye.

BACKGROUND

Age-related Macular degeneration (AMD) is a medical condition that affects the center of retina (macula) in elderly patients and is leading to loss of central vision. Peripheral visual field is usually not affected and patients keep ability for orientation. Nonetheless most patients loose the ability to read at least in the late stage of the disease. AMD is the leading cause for blindness and visual impairment in patients older than 50 years in the western world.

Numerous surgical interventions with implantation of special lenses and devices have been proposed. Some systems rely on magnification of the image, but at the same time cause severe reduction of the visual field, like the implantable telescopic lens system described in EP1475055. This solution did not become popular because of the reduction of the visual field and because it is bulky and difficult to implant. Also, it is contraindicated in single eyed patients.

Other systems using Fresnel Lens systems, like described in patent application WO2005039451 or combined converging and diverging lenses with non-coincident axes, like described in patent applications WO2010136798 and WO2010131955, proposed to optically divert the light beam and displace the focus to an area of the retina outside the fovea. These systems also did not become popular because displacing the focus to other areas of the retina than the fovea does not allow reading vision as these parts of the retina have a reduced intensity of photoreceptor cells.

Other systems proposed the combination of special intraocular implants having at least one negative intraocular lens portion interacting with an external lens (spectacles) as described in patent applications WO0132105 and EP2319457. These systems did not become popular because the use of special spectacles is required, therefore they do not offer any advantage over classical magnification glasses.

Patent applications WO8707496 and WO8909576 describe a one-piece bifocal intraocular lens construction. However, these lenses are described as stand-alone lenses that are not designed as a secondary IOL optically co-operating with a primary IOL. Further, aforementioned lenses are described as rigid lenses. Finally, the power distribution of the lenses in the aforementioned documents is limited to the use for presbyopia claiming addition of 2-4 diopters in the central lens portion for near vision.

The main problem with all aforementioned inventions is that the systems proposed are usually designed to be implanted instead of a standard intraocular lens, and most surgeons would object to that choice.

As a matter of fact, more than two thirds of patients with advanced AMD and visual acuity of 0.3 or less are pseudophakic already, i.e. they have had cataract surgery with implantation of an intraocular lens into the capsular bag.

If the intraocular lens already implanted within the capsular bag is to be retained then any corrective additional intraocular lens needs to be positioned anterior to the capsular bag, hence either in the anterior chamber of the eye or in the posterior chamber, between the pupil and the capsular bag, in the ciliary sulcus. Implanting an intraocular lens in the anterior chamber is not recommended in case of patients who have glaucoma, a shallow anterior chamber, insufficient iris tissue, or corneal endothelial dystrophy. Ciliary sulcus implantation is not possible with bulky telescopic lens systems of the prior art because there is not enough space between the capsular bag and the pupil/iris.

A further problem associated with ciliary sulcus implantation is the so-called pupillary capture (or iris capture) when the IOL is implanted in the ciliary sulcus. Pupillary capture is defined as dislocation or entrapment of all or part of an IOL optic through the pupillary aperture. Postoperative pupillary capture of the IOL optic can occur for a variety of reasons like improper placement of the IOL haptics, shallowing of the anterior chamber, or anterior displacement of the posterior chamber IOL optic, and it is much more common in case of ciliary sulcus IOLs than capsular bag IOLs due to the proximity of the pupil.

Pupillary capture can cause problems with glare, photophobia, chronic uveitis, unintended myopia, or even monocular diplopia as well as excessive pain in extreme cases. Mydriatics can sometimes be used successfully to free the iris through pharmacologic manipulation of the pupil. If conservative management fails, surgical intervention may be required to free the iris or reposition the IOL.

It is an objective of the present invention to provide a simple, inexpensive and safe solution for improving the near vision of patients, in particularly pseudophakic patients suffering from Age-related Macular Degeneration (AMD) by implanting a secondary intraocular lens in the ciliary sulcus anterior to a primary intraocular lens already implanted within the capsular bag.

SUMMARY

The inventors have realized that it is possible to benefit from the effect of near vision miosis in which the pupil constricts reflexively when the eye focuses on a near object. This reflex also works reliably in elderly people. The constriction of the pupil limits the light beam to the center of the lens in the eye.

The present invention is designed to correct the near vision of pseudophakic patients suffering from AMD, in particular dry AMD, by making use of miosis as one of the three natural eye reflexes being part of the so-called Near Triad (Accommodative Triad), i.e. the decrease in size of the pupil that accompanies accommodation and convergence of the two eyes.

The inventors have also realized that with appropriate design of the IOL optic and the IOL haptics it is possible to prevent pupillary capture of an IOL implanted in the ciliary sulcus.

Accordingly, the invention relates to a method of implanting a secondary intraocular lens, IOL, that is made from a foldable soft material like acrylate or silicone. The method of implanting includes the steps of implanting a secondary IOL, having an optically active lens part containing a central optical lens portion and having a plurality of evenly spaced haptics around the optically active lens part, between an iris of the eye and a capsular bag containing at least one primary IOL, placing the central optical lens portion of the secondary IOL in an aligned position optically coaxial to the at least one primary IOL for magnifying and focusing an image projected by the central lens portion through the at least one primary IOL on a fovea of a retina of the eye, and fixing the secondary IOL in the aligned position by arranging the plurality of haptics behind the iris in a ciliary sulcus of the eye.

Preferably, the iris is spaced from the primary IOL by introducing an ophthalmic viscosurgical device under the iris prior to implantation of the secondary IOL.

The secondary IOL is designed to be surgically implanted into the ciliary sulcus of a patient's pseudophakic eye, i.e. in addition to at least one primary IOL that has already been implanted in the posterior chamber of the patient's eye prior to the implantation of said secondary IOL.

The secondary IOL is designed to optically co-operate with the primary IOL in order to coaxially focus a combined image on the retina of the patient's eye thereby improving the visual capabilities of the patient by additionally magnifying at least a central part of the image of the primary IOL projected onto the fovea of the retina. Near vision is enhanced as a result.

The foldable secondary IOL comprises an optically active lens part having an optical axis designed to project the image through the primary IOL onto the retina and at least two haptics for fixing the IOL within the ciliary sulcus of the patient's eye.

The secondary IOL is implanted between a pupil of the eye and the capsular bag containing the at least one primary IOL. The central optical lens portion of the secondary IOL is aligned so as to be optically coaxial to the at least one primary IOL for magnifying and focusing on a fovea of a retina of the eye an image of a near object, which magnified image is projected through the at least one primary IOL by the central optical lens portion. A near object is an object located 5 to 20 cm from the eye, and the image is magnified compared to an image that would be produced without the presence of the secondary IOL.

The plurality of haptics is arranged in the ciliary sulcus for fixing the secondary IOL in the coaxially aligned position.

Particularly preferred optically active lens part has at least four haptics unitary with the optically active lens part and evenly spaced about the periphery of the optically active lens part. The periphery of the optically active lens part has a non-convex rim between any two neighboring haptics, which is free from surface irregularities (projections and/or recesses) that interfere with the iris of the eye in order to prevent iris capture, which is a common problem associated with prior art sulcus lenses. Preferably, a cross-section of the rim is non-convex, i.e., concave or straight. The rim of the optically active lens part may have projections or recesses as long as such surface irregularities are small enough not to allow the iris of an eye to be captured thereon or therein, respectively. Preferably such projections or recesses have a radius smaller than 1.5 mm, more preferably smaller than 0.6 mm, most preferably smaller than 0.3 mm.

The central optical lens portion preferably has a diameter smaller than 1.8 mm, and the central optical lens portion and the peripheral optical lens portion form two different, but coaxially positioned lenses manufactured either from a single block of uniform material, or by combining two separate lenses into one block.

The central optical lens portion is designed to form a positive lens providing additional refraction of preferably more than +5 diopters to the refraction provided by the peripheral optical lens portion of the secondary IOL, whereby the combined refractive power of the central optical lens portion of the secondary IOL and a corresponding central portion of the primary IOL provides additional refraction of more than +5 diopters compared to the combined refraction of the peripheral optical lens portion of the secondary IOL and a corresponding peripheral portion of the primary IOL.

In this manner, the patient is provided with the ability to have a magnified central image without using spectacles or magnifying glass. If the patient is not satisfied with the secondary IOL, it can be removed surgically while keeping the function of the primary IOL. Due to the effect of near vision miosis, the central optical lens portion—providing the magnified central part of the image—will perform when the patient focuses on near objects only but will not influence significantly the far vision when the patient focuses on distant objects through a dilated pupil.

The present invention targets pseudophakic patients with advanced AMD, offering them a convenient, simple and safe solution to restore their near vision impaired by AMD.

Further advantageous embodiments of the invention are defined in the attached dependent claims.

BRIEF DESCRIPTION OF THE DRAWINGS

Further details of the invention will be apparent from the accompanying figures and exemplary embodiments.

FIG. 3 is a schematic sectional view in the median plane of the secondary IOL shown in FIG. 1.

FIG. 6 is a schematic back view of another preferred secondary IOL showing a non-deformed state of four haptic loops with solid line and illustrating a deformed state of the haptic loops with dashed line.

FIG. 7 is an enlarged schematic view of one haptic loop according to FIG. 6 showing the non-deformed state with solid line and the deformed state with dashed line.

FIG. 10 is a side view of another preferred secondary IOL.

DETAILED DESCRIPTION

Figure 2:
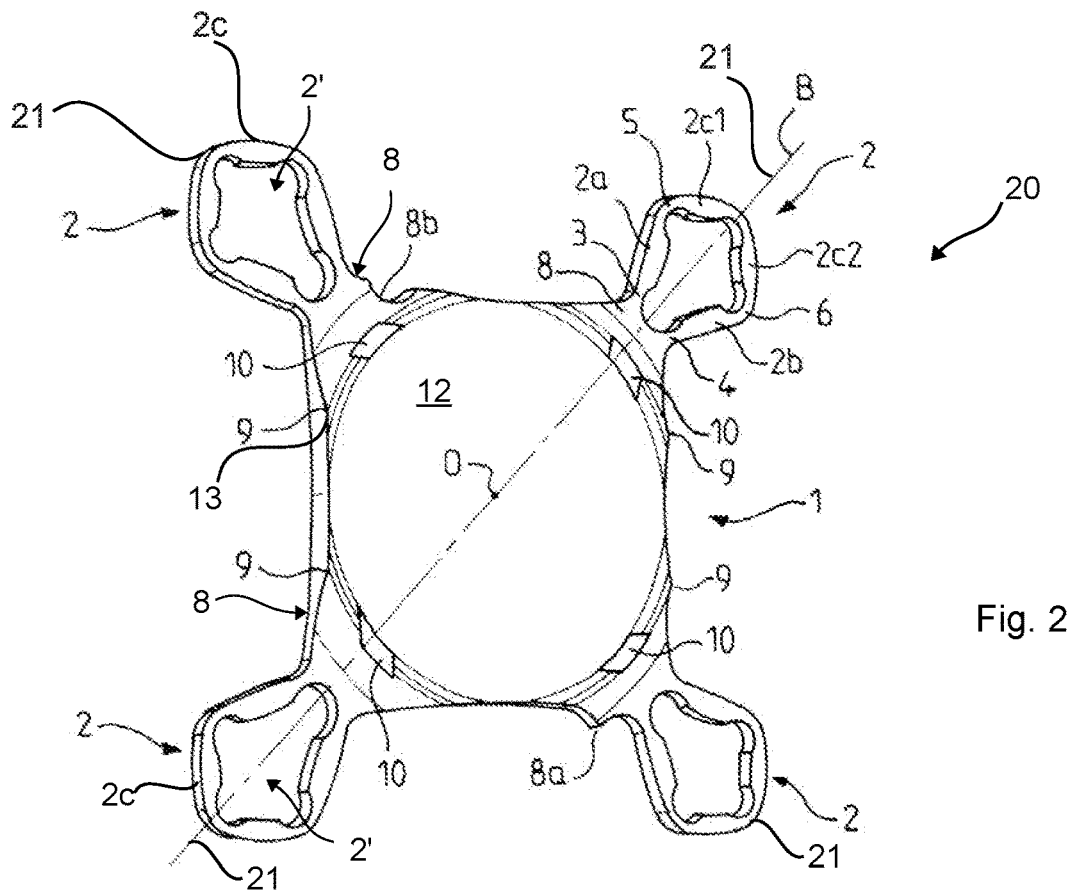
FIG. 2 is a schematic perspective back view of the secondary IOL.
Figure 1:
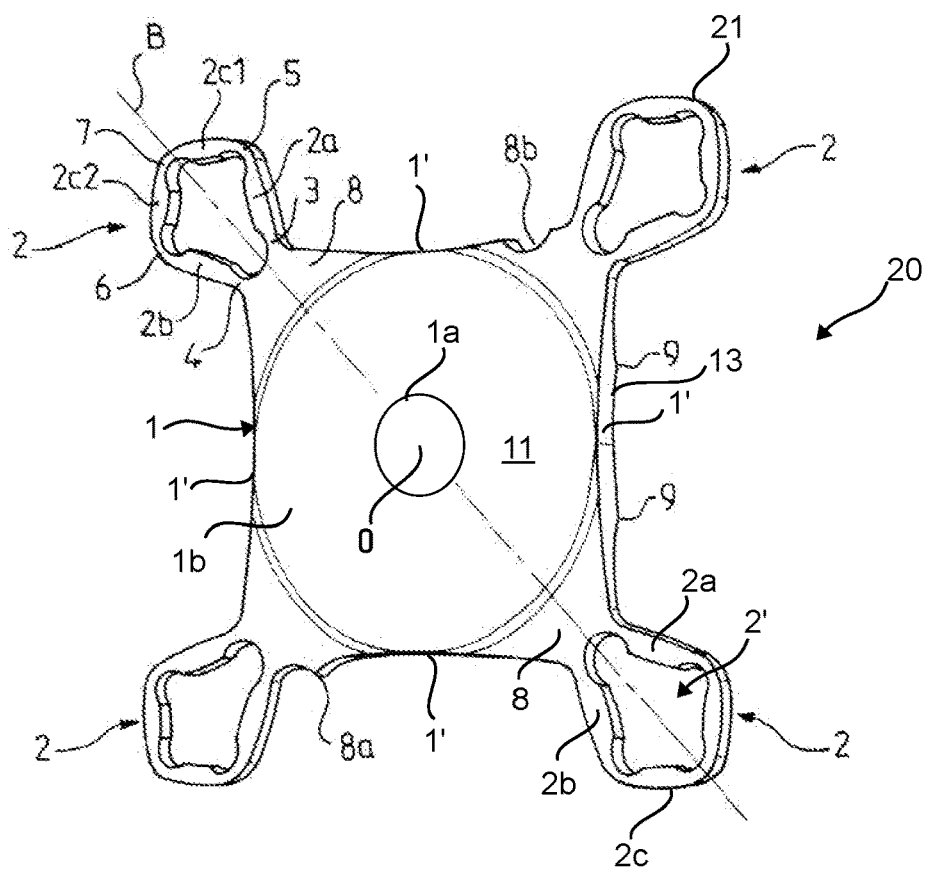
FIG. 1 is a schematic perspective front view of a preferred secondary IOL for use in the claimed method.

FIGS. 1-3 schematically illustrate a secondary intraocular lens, IOL, 20 for use in the claimed method by implantation in a ciliary sulcus of an eye. The IOL 20 is made from a foldable soft material such as acrylate or silicone. The IOL 20 comprises an optically active lens part 1 and four haptics 2, formed with loops 2a, unitary with the optically active lens part 1 and uniformly spaced about a periphery of the optically active lens part 1 for fixing and stabilizing the IOL 20 within a patient's eye and.

The optically active lens part 1 has a central optical lens portion 1a and a peripheral optical lens portion 1b unitary with the central optical lens portion 1a and surrounding it.

The central optical lens portion 1a and the peripheral optical lens portion 1b form two different, but coaxially positioned lenses with a common optical axis O. The central optical lens portion 1a and the peripheral optical lens portion 1b can be made either from a single piece of uniform material, or by arranging two separate lenses to form a multi-piece optically active lens part 1.

The central optical lens portion 1a is designed to form a positive lens providing additional refraction to the refraction provided by the peripheral optical lens portion 1b of the secondary IOL 20. The additional refraction of the central optical lens portion 1a over the peripheral optical lens portion 1b may be more than +5 diopters in order to produce a magnification that could restore the patient's reading capability. The additional refraction of the central optical lens portion 1a over the peripheral optical lens portion 1b may be less than +25 diopters because in real life it would be hard to handle any object closer to the eye than 4 cm. The central optical lens portion 1a preferably has a refractive power that differs from the peripheral optical lens portion's refractive power by +5 diopters up to +25 diopters, more preferably by +5 diopters up to +12 diopters, even more preferably +8 diopters up to +12 diopters. Accordingly, when the secondary IOL 20 is used in combination with a primary IOL 30 of uniform refraction (e.g. a traditional positive lens) as will be explained later on, the central optical lens part 1a provides additional refraction of between +5 diopters and +25 diopters, preferably between +5 diopters and +12 diopters, more preferably between +8 diopters and +12 diopters compared to the combined refraction of the primary IOL 30 and the peripheral optical lens portion 1b of the secondary IOL 20.

The peripheral optical lens portion 1b may be designed to form a lens with zero refraction, thus when the secondary IOL 20 is implanted adjacent a conventional biconvex primary IOL 30 it does not affect the image provided by a corresponding peripheral portion of the primary IOL 30. In another suitable secondary IOL 20 the peripheral optical lens portion 1b may be designed to form a lens with a given refraction between −5 diopters and +15 diopters in order to correct any error in refraction or any unintended, undesired change in the patient's vision provided by the primary IOL 30.

The optically active lens part 1 preferably has a diameter between 4 and 10 mm, more preferably between 5 and 7 mm.

The ratio between the diameters of the central optical lens portion 1a and the optically active lens part 1 of the secondary IOL 20 is preferably between 0.05 and 0.45, more preferably between 0.15 and 0.35.

The diameter of the central optical lens portion 1a is preferably smaller than 1.8 mm in order to fully use but not to exceed the diameter of the constricted pupil (by much) and in order not to disturb far vision through the dilated pupil in a significant way. The central optical lens portion 1a preferably has a diameter bigger than 0.5 mm in order to produce the minimal desired magnifying effect that can be perceived by the patient. More preferably, the central optical lens portion 1a has a diameter between 0.8 mm and 1.6 mm in order to produce a sound balance between the above mentioned conditions.

Figure 12:
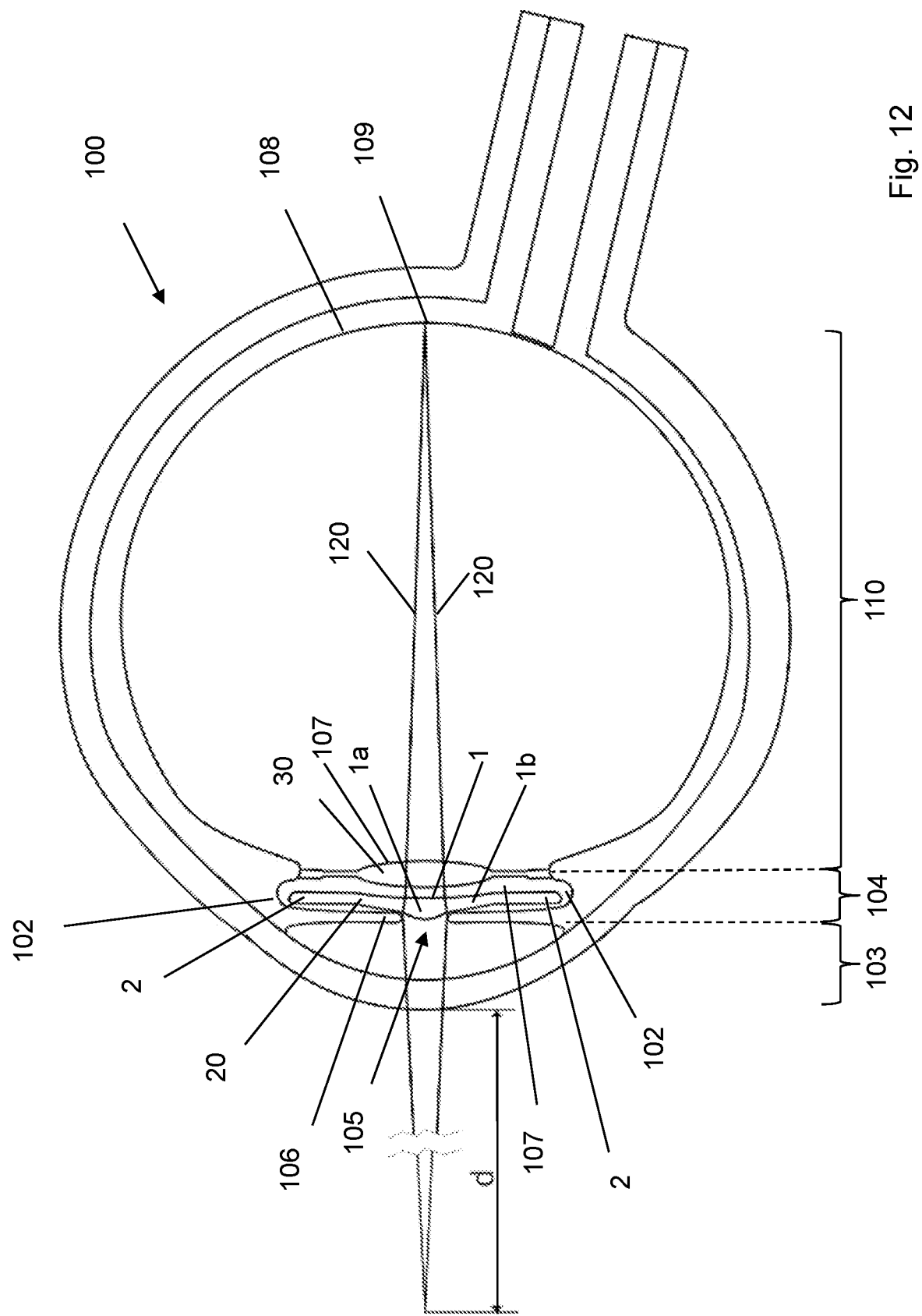
FIG. 12 is a schematic cross-sectional view of the secondary IOL and the primary IOL implanted in an eye and illustrating light rays passing through the two lenses during near vision.
Figure 13:
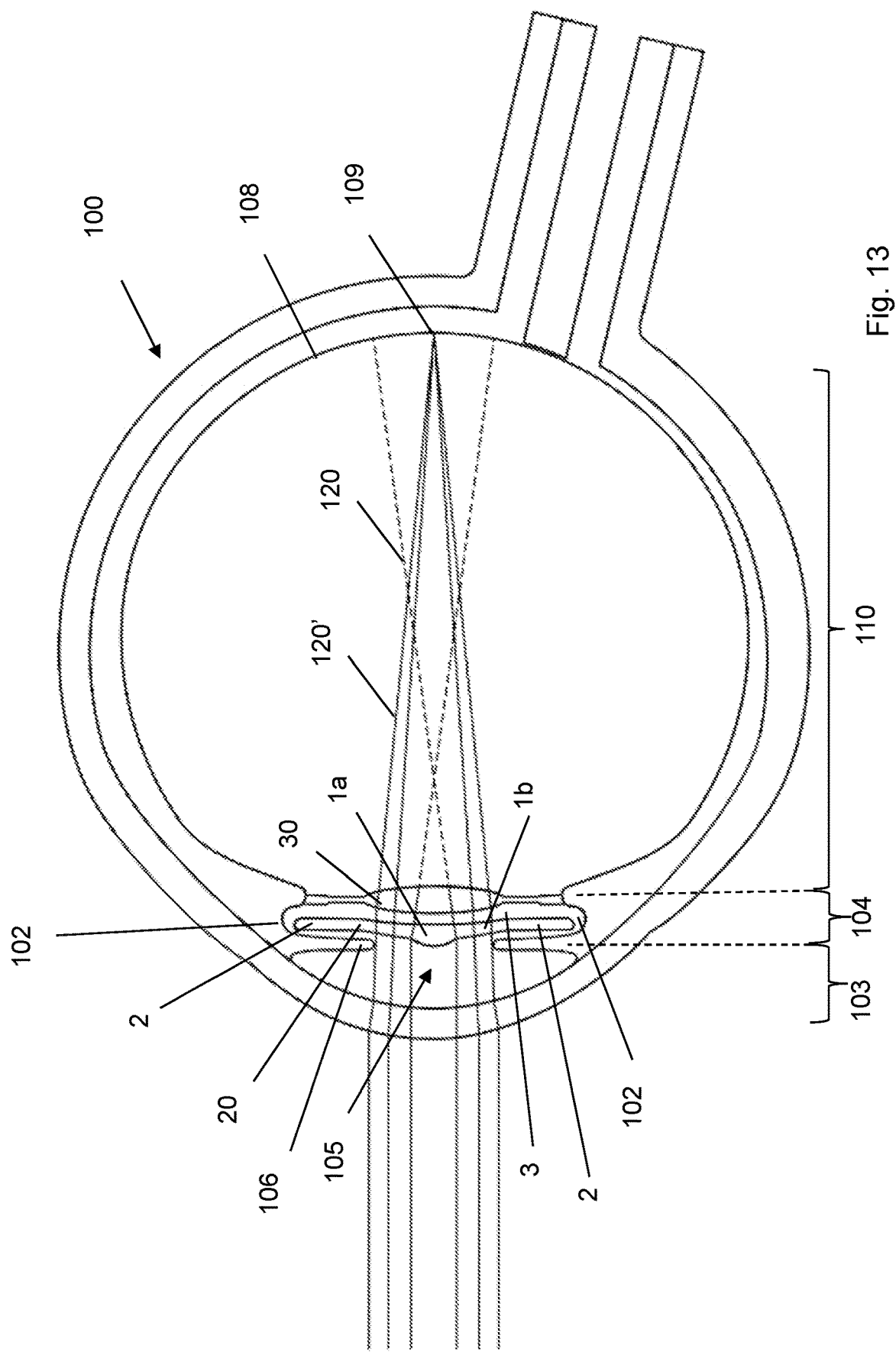
FIG. 13 is a schematic cross-sectional view of the secondary IOL and the primary IOL implanted in an eye and illustrating light rays passing through the two lenses during far vision.

The secondary IOL 20 is surgically implanted into a ciliary sulcus 102 of an eye 100 as illustrated in FIGS. 12 and 13. The eye 100 contains an anterior chamber 103 and a posterior chamber 104, which are separated by a pupil 105 formed by an iris 106 of the eye 100. The ciliary sulcus 102 lies in the posterior chamber 104 between the iris 106 and a capsular bag 107, which normally contains the natural lens of the eye 100. A vitreous chamber 110 (also called posterior cavity) is located behind the capsular bag 107 and is filled with a vitreous gel. The back of an inner wall of the vitreous chamber is lined with a special layer of cells (cone cells and rod cells) forming a retina 108. Both color vision and highest visual acuity is attributed to cone cells. Rod cells are responsible for night vision, most sensitive motion detection, and peripheral vision. At its center the retina 108 contains a macula, which processes sharp, clear, straight-ahead vision. Fovea (fovea centralis) 109 is a pit or depression at the center of the macula that provides greatest visual acuity because cone cells are concentrated in the fovea 109. The fovea 109 corresponds to the clinical macula, which is the part of the anatomical macula that is seen through the pupil 105. Rods are absent from the fovea 109 but abundant elsewhere in the retina, hence the rest of the retina 108 provides side (peripheral) vision, which allows shapes to be seen but not fine details.

In case of a pseudophakic eye 100 the natural crystalline lens has been removed and replaced by the primary IOL 30, which is generally implanted within the capsular bag 107 as this is believed to be the most ideal place for an IOL.

The eye 100 further comprises a cornea 112, which is a transparent structure at the front of the eye 100 that covers the iris 106, pupil 105 and anterior chamber 103; it is the eye's 100 primary light-focusing structure.

The secondary IOL 20 lies adjacent the pupil 105 when implanted in the ciliary sulcus 102 which makes it prone to pupillary capture. Pupillary capture occurs when part of the pupil's 105 margin, the iris 106 is displaced posteriorly behind the IOL optic, which then appears to lie in the anterior chamber 104 of the eye 100. In order to prevent pupillary capture, the secondary IOL 20 has four haptic loops 2' and a rim 1' of the optically active lens part 1 is non-convex (concave and/or straight) between any two neighboring haptic loops 2. The rim 1' of the optically active lens part 1 may, however, have minor projections or recesses (e.g. for the purpose of positioning) which are small enough (preferably smaller than 1.5 mm, more preferably smaller than 0.6 mm, most preferably smaller than 0.3 mm) so as to prevent the iris 106 to be captured thereon or therein, respectively.

Pupillary capture is preferably further prevented by providing each haptic 2 with a flat, thin, generally triangular shoulder 8 forming a transition between the optically active lens part 1 and the haptic loop 2'. The shoulders 8 are of generally triangular shape and have a thickness of about 0.2 mm. The generally triangular shape means that the shoulders 8 narrow in the direction of the haptic loops 2, preferably as a continuation of the concave or straight rim 1' of the optically active part 1 and thereby have the effect of avoiding a risk of the iris 106 being caught by the haptic loops 2. The shoulders 8 have a cross-section that generally decreases in the direction of the loop 2' extending therefrom. The shoulders 8 may be provided with a lateral projection 8a and/or a recess 8b for performing a positioning function as long as such projection 8a and recess 8b is small enough to prevent the iris 106 to be captured thereon and therein, respectively. Alternatively, such a projection and/or recess may be formed on the rim 1' of the optically active lens part 1.

The design of the haptic loop 2' further contributes to preventing pupillary capture.

The IOL 20 has four haptics 2 regularly distributed around the optically active lens part 1. Since the haptics 2 are identical, the reference numbers have not been placed on all of them, in order not to complicate the drawing.

The haptic loops 2' form two diametrically opposed pairs, one pair being arranged along a median transverse axis B passing through the optical axis O, the other pair being arranged transversal to axis B.

The loops 2' preferably have a symmetric shape the axis of symmetry preferably corresponding to a diameter of the IOL 20 passing through poles 21 of two opposing loops 2'. One such axis of symmetry corresponds to the median transverse axis B indicated in FIGS. 1 and 2. This symmetric haptic shape eliminates any torque acting on the IOL 20 after implantation in the ciliary sulcus 102, whereby the IOL 20 will not be prone to rotation around the optical axis O of the optically active lens part 1 which is important if the optic is designed to have a toric shape in order to correct for astigmatism in a way known in the art. In the case of a toric optically active lens part 1 the refractive power of the central optical lens portion 1a and of the spherical optical lens portion 1b is understood to correspond to the spherical power of each lens portion 1a, 1b for spherical correction, not including the diopters for astigmatism correction.

Each loop 2' is formed by two lower segments 2a, 2b which, at one end, are connected by two lower elastic flexion points 3, 4 to the shoulder 8 of the haptic 2, and, at the other end, are connected by two upper elastic flexion points 5, 6 to opposed end portions of an upper segment 2c. The upper segment 2c comprises two parts 2c1, 2c2, which are joined to each other by a further elastic flexion point 7. The outer edge of the lower segments 2a, 2b of each loop is preferably, generally straight. The elastic flexion points 3, 4, 5, 6, 7 allow for the elastic deformation of the loops 2', other portions of the loop 2' are preferably more ridged in order to ensure that upon compression any flexion of the loops 2' occurs at the flexion points 3, 4, 5, 6, 7.

Figure 5:
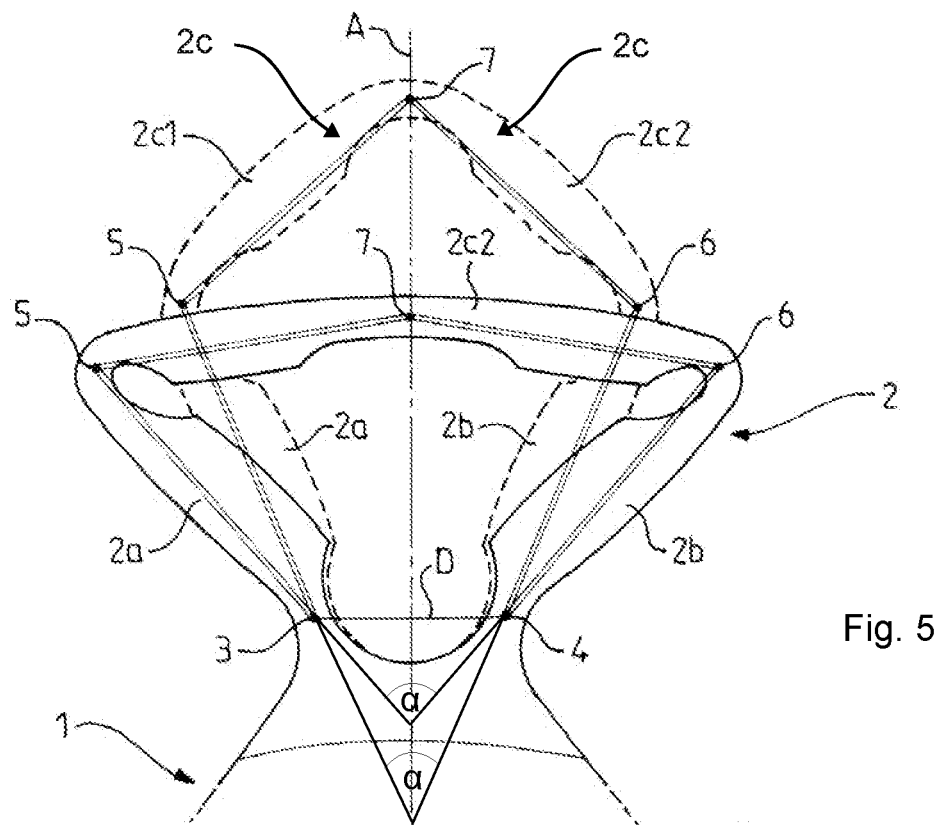
FIG. 5 is an enlarged schematic view of one haptic loop showing the non-deformed state with solid line and the deformed state with dashed line.
Figure 4:
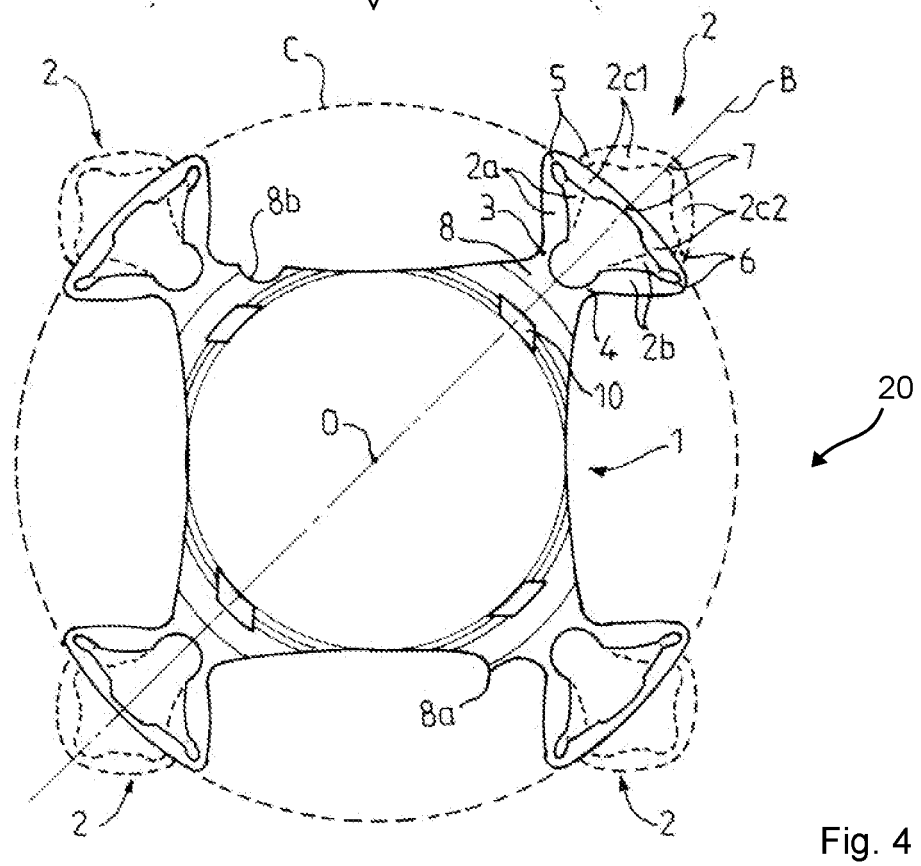
FIG. 4 is a schematic back view of the secondary IOL showing a non-deformed state of four haptic loops with solid line and illustrating a deformed state of the haptic loops with dashed line.

FIG. 4 provides a schematic illustration of the haptic loops 2' at a non-deformed rest position (broken lines) and in the state of maximum deformation (solid lines). FIG. 5 is an enlarged view of one loop 2' with a skeleton diagram laid thereover in order to facilitate the understanding of the deformation. The lower flexion points 3, 4 are spaced from each other by a distance D (see FIG. 5), such that they converge in the direction of the optically active lens part 1 and diverge in the direction of the upper segment 2c with respect to the median vertical axis A passing through the pole of a haptic loop 2' and through an optical axis O of the lens. The sum of the lengths of the lower segments 2a, 2b and of the distance D is greater than the length of the upper segment 2c. Under the effect of compression forces acting on the pole of the loop 2', which is substantially at the flexion point 7, in the direction of the optically active lens part 1, the pivoting of the lower segments 2a, 2b in a plane perpendicular to the optical axis O produces the displacement of the upper flexion points 5, 6 in the direction of the optically active lens part 1 and the flattening of the upper segment 2c by pivoting of the upper segment parts 2c1, 2c2 around the upper flexion point 7 as illustrated in FIGS. 4 and 5.

Under the effect of the compression forces exerted on the haptic loops 2', the latter deform with a gradual flattening movement of the upper segments 2c1, 2c2 and spacing-apart of the lower segments 2a, 2b about flexion points 3, 4, 5, 6 and 7. Thus the two lower segments 2a, 2b and the upper segment 2c of each loop 2' are configured to occupy a non-deformed state in which the lower segments 2a, 2b are lying at a first angle to each other and the upper flexion points 5, 6 are at a first distance from each other, and an elastically deformed state in which the arched upper segment 2c flattens, the lower segments 2a, 2b are lying at a second angle to each other and the upper flexion points 5, 6 are at a second distance from each other, the second angle being greater than the first angle and the second distance being greater than the first distance.

The size ratio of the lower segments 2a, 2b with respect to the upper segments 2c1, 2c2, their spacing of distance D from each other and their convergence in the direction of the optically active lens part 1, preferably in the direction of the optical axis O, ensure that the movement of deformation does not go beyond a return point at which the upper segments 2c1, 2c2 are substantially in alignment with each other. Accordingly, by design, the haptic loops 2' cannot continue to deform beyond the lower position shown in FIGS. 4 and 5 with solid line.

In this way a haptic loop 2' is obtained that can deform elastically in the direction of the optically active lens part 1 by a limited distance, this deformation being blocked when a maximum opening angle $\alpha$ of the lower segments 2a, 2b is reached. The maximum opening angle $\alpha$ is preferably between 70° to 170°, more preferably between 70° to 130°. In practice, the loop 2' ceases to deform any further when fully abutting the circular perimeter of the ciliary sulcus 102. The maximum flattening of the upper segments 2c is reached when the outer edge of each upper segment 2c follows the curvature of circle C indicated with a dashed line in FIG. 4. Accordingly, the circle C symbolizes the position of maximum compression of the haptic loops 2. In practice, the dimensions of the IOL 20 are chosen such that the diameter of the circle C will be between 10.5 mm and 12.5 mm, which corresponds to the overall diameter of the IOL 20, in the state of maximum compression of its haptic loops 2'.

The lower segments 2a, 2b preferably have a length of the order of 1.6 mm, and the upper segments 2c1, 2c2 a length of the order of 1.4 mm. The flexion points 3, 4, 5, 6 and 7 are preferably obtained by reducing the cross section of the material from which each haptic loop 2' is made.

The secondary IOL 20 is designed to be implanted in the ciliary sulcus 102 of an eye anterior of a primary IOL 30 implanted in the capsular bag 107 (see schematic illustration in FIGS. 12, 13). FIG. 6 illustrates the position of the secondary IOL 20 with respect to the primary IOL 30, which generally comprises an optically active lens part 31 and haptics 32. In order to adapt to the anterior face of the primary IOL 30 present in the capsular bag 107 the optically active lens part 1 is preferably concavo-convex as can be best seen in FIG. 3. In order to ensure that a space permitting circulation of the aqueous humor is maintained between the adjacent faces of the optically active lens parts 31 and 1 of the primary IOL 30 and of the secondary IOL 20, the secondary IOL 20 has four projections or stubs 9 arranged regularly on a posterior edge 13 of a posterior face 12 of the optically active lens part 1. For this same purpose, recesses 10 are additionally arranged along the perimeter of the posterior face 12 of the optically active lens part 1 and substantially centered on the diameters passing through the poles of the haptic loops 2.

FIG. 7 illustrates a modified IOL 20 with respect to the IOL 20 shown in FIGS. 1 to 5, in which the outer edges of the upper segments 2c1, 2c2 of the haptic loops 2' are formed with ridges 7. This arrangement permits a better engagement of this part of the haptic loops with an internal periphery of the ciliary sulcus 102 and, as such, a better fixation of the IOL 20.

Figure 9:
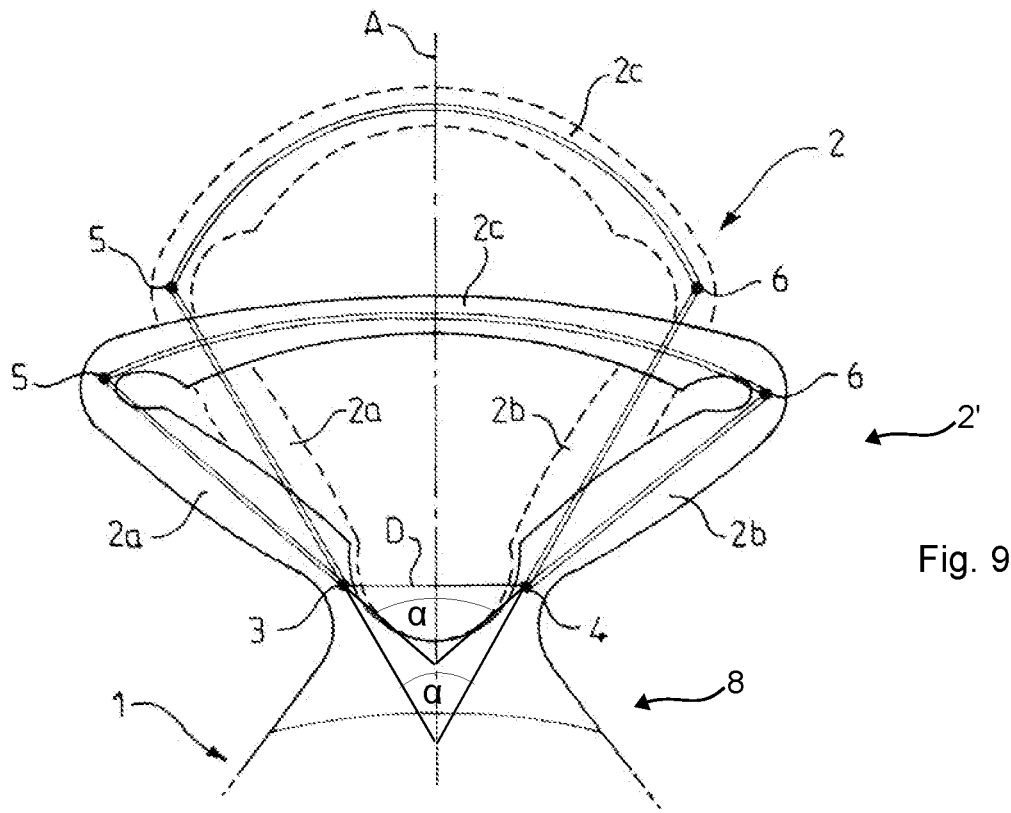
FIG. 9 is a schematic perspective view of the secondary IOL according to FIG. 1 arranged in a proximal position in front of a primary IOL.
Figure 8:
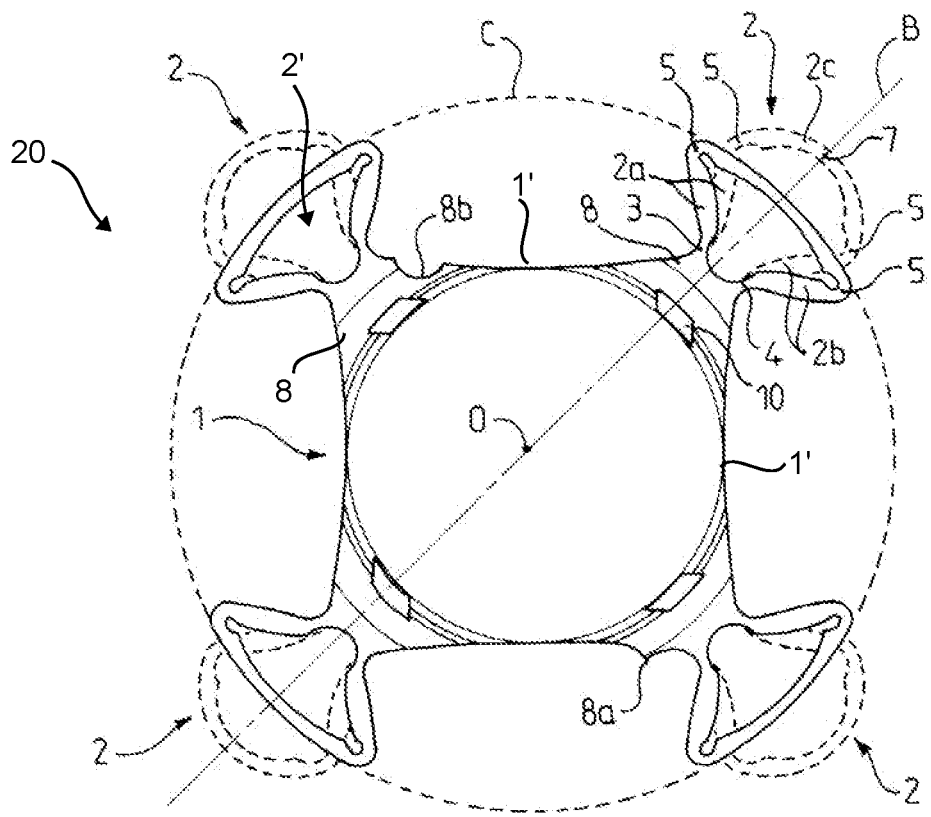
FIG. 8 is a schematic back view of another preferred secondary IOL.

FIGS. 8 and 9 show a schematic view of a suitable secondary IOL 20, having a different haptic loop 2 design than the previously described IOLs 20. The haptic loops 2 are illustrated at rest (broken lines) and in the state of maximum deformation (solid lines). In contrast to the IOL 20 shown in FIGS. 1 and 2, the upper segment 2c of the haptic loop 2 is formed as a single arched segment 2c without any flexion points separating it. All the other features of the IOL 20 are similar and are designated by the same reference numerals. The upper segment 2c is elastic and arched such that, under the effect of the compression forces acting in the direction of the optically active lens part 1, the pivoting of the lower segments 2a, 2b in a plane perpendicular to the optical axis O produces the lowering of the upper flexion points 5, 6 and the flattening of the elastic upper segment 2c. Elastic deformation of the loops 2' occurs not only at the flexion points 3, 4, 5, 6 but also in the upper segment 2c. As depicted in FIGS. 4 and 5, the haptic loop 2' cannot continue to deform beyond the lower position indicated in FIGS. 8 and 9 with solid lines.

The elastic flexion points 3, 4, 5, 6, 7 allow for the elastic deformation of the loops 2', other portions of the loop 2' are preferably more ridged in order to ensure that upon compression any flexion of the loops 2' occurs at the flexion points 3, 4, 5, 6, 7.

Similarly to the previously described IOLs, this is also an additional IOL 20 for positioning in the ciliary sulcus 102 in front of a capsular bag IOL 30. It can likewise be made with a ridged contour on the outer edge of the upper segments 2c via which the haptic loops 2' abut the internal periphery of the ciliary sulcus 102.

Figure 11:
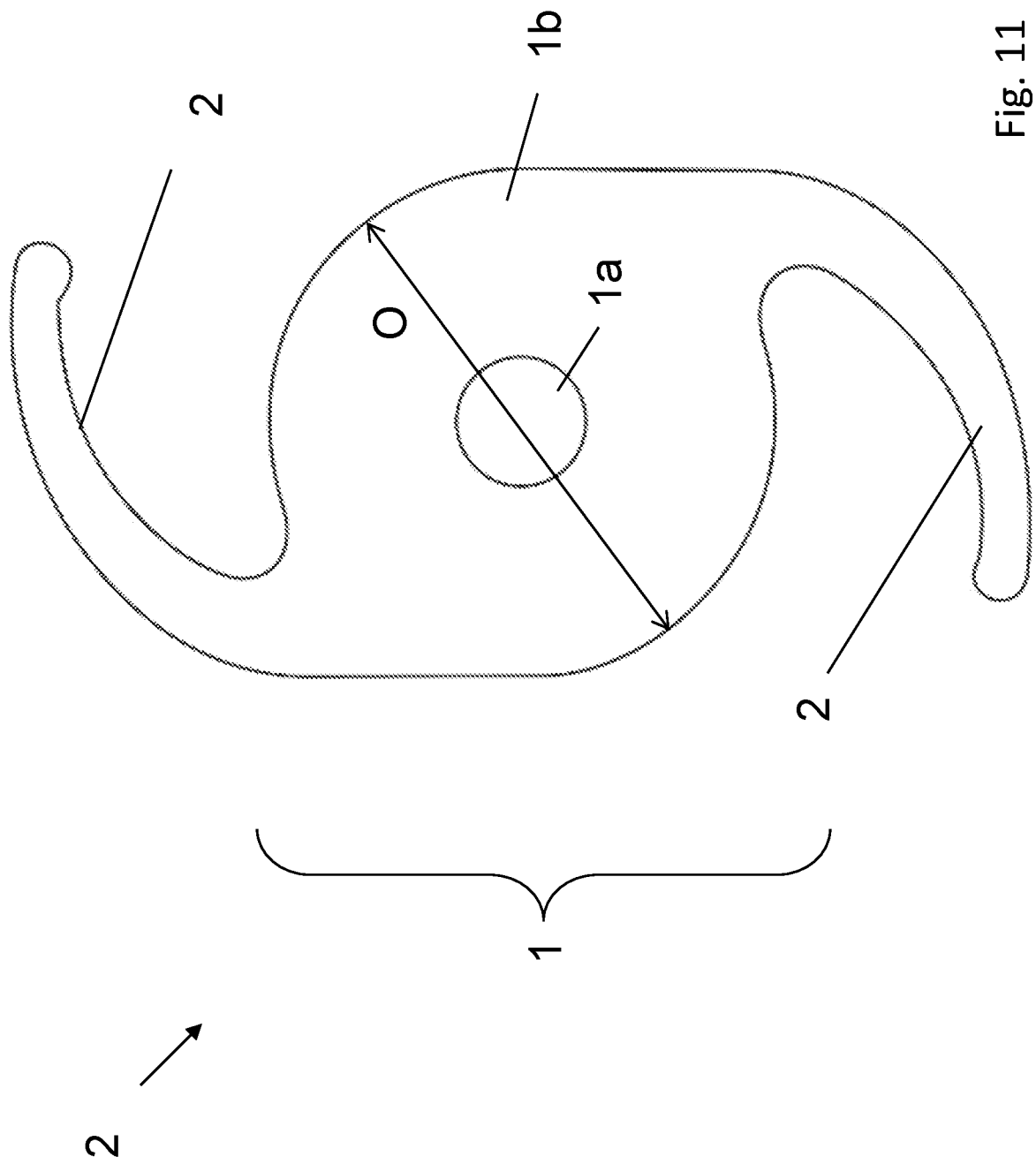
FIG. 11 is a front view of the secondary IOL shown in FIG. 10.

FIGS. 10 and 11 show yet another secondary IOL 20 comprising two open C-shaped haptics 2 formed integrally with the optically active lens part 1. It is noted that the haptics 2 could have any other suitable design such as Z-shaped loop, closed loops or plate haptics with or without fenestration, with or without axial angulation.

The optically active lens part 1 comprises a central optical lens portion 1a and a peripheral optical lens portion 1b extending around the central optical lens portion 1a. The central optical lens portion 1a and a peripheral optical lens portion 1b form two different, but coaxially positioned lenses from one block. The optically active lens part 1 may have a diameter O between 4 mm and 10 mm, preferably between 5 mm and 7 mm.

The central optical lens portion 1a is designed to form a positive lens providing additional refraction to the refraction provided by the peripheral optical lens portion 1b of the secondary IOL 20.

The diameter of the central optical lens portion 1a may be smaller than 1.8 mm in order to fully use but not to exceed the diameter of the constricted pupil (by much) and not to disturb far vision through the dilated pupil in a significant way. The central optical lens portion 1a preferably has a diameter greater than 0.5 mm in order to produce the minimal desired magnifying effect that can be perceived by the patient. Preferably the central optical lens portion 1a has a diameter between 0.8 mm and 1.6 mm in order to produce a sound balance between the above-mentioned conditions.

The additional refraction of the central optical lens portion 1a over the peripheral optical lens portion 1b is more than 5 diopters in order to produce a magnification that could restore the patient's reading capability. The additional refraction of the central optical lens portion 1a over the peripheral optical lens portion 1b is less than 25 diopters because in real life it would be hard to handle any object closer to the eye than 4 cm. Therefore, the central optical lens portion 1a may have a refractive power of between +5 diopters and +25 diopters, preferably between +8 diopters and +12 diopters in addition to the refractive power of the peripheral optical lens portion 1b. Thus, when the secondary IOL 20 is implanted adjacent a conventional biconvex primary IOL 30, the combined refraction of the primary IOL 30 and the central optical lens portion 1a of the secondary IOL 2 is +5 diopters to +25 diopters greater, preferably +8 diopters to +12 diopters greater than the combined refraction of the primary IOL 30 and the peripheral optical lens portion 1b of the secondary IOL 20.

The peripheral optical lens portion 1b may be designed to form a lens with zero refraction, thus not interfering with the image provided by the primary IOL 1, leaving the patient most of his vision provided by the primary IOL 1. In another secondary IOL 20 the peripheral optical lens portion 1b may be designed as a lens having a refractive power between −5D and +15D in order to correct any existing error in refraction or any unintended, undesired change in the patient's vision provided by the primary IOL 1.

The ratio between the diameters of the central optical lens portion 1a and the optically active lens part 1 of the secondary IOL 20 may be between 0.05 and 0.45, preferable between 0.15 and 0.35.

Figure 14:
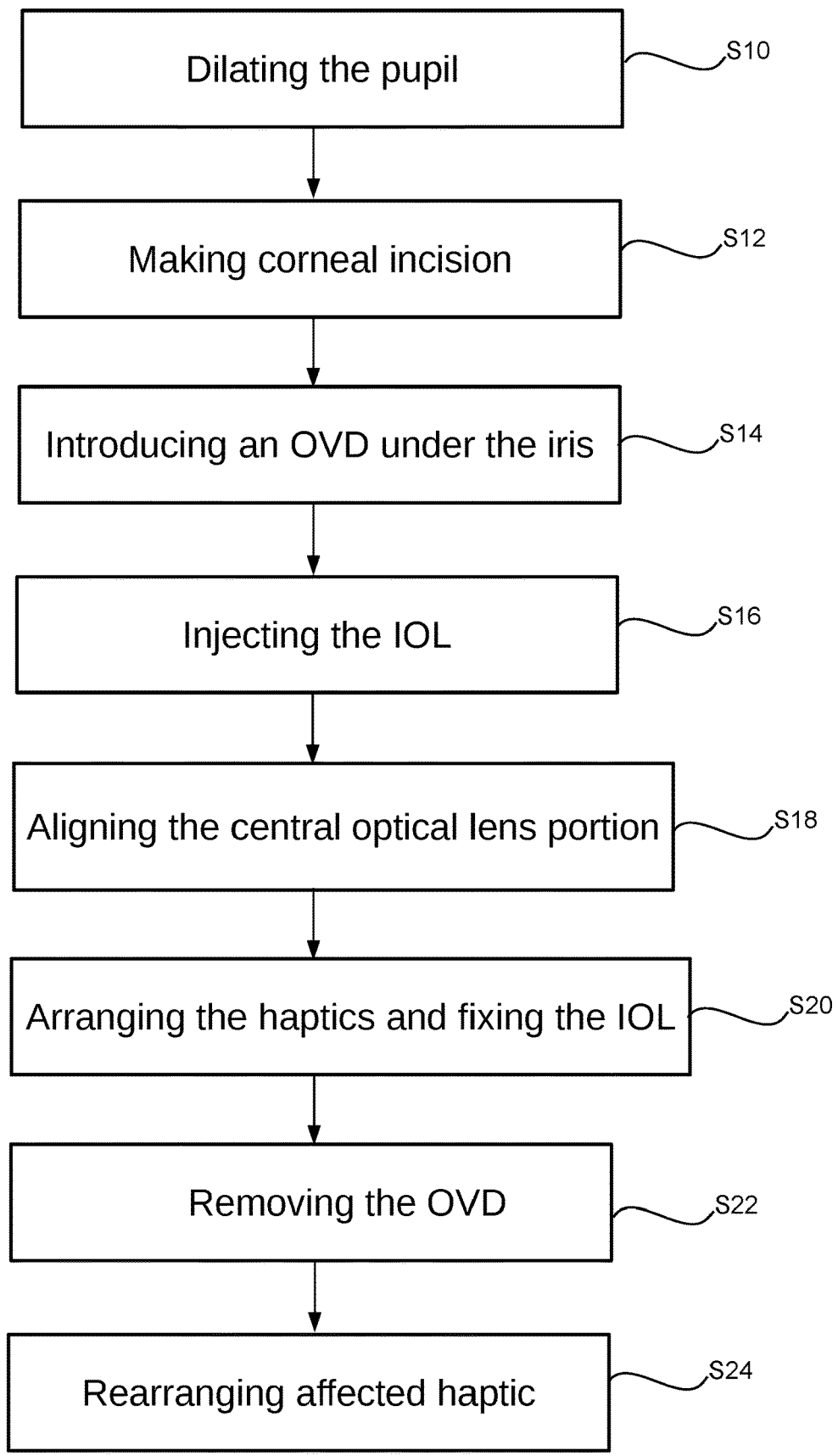
FIG. 14 is a flow diagram of a preferred method according to the invention.

In the following a preferred method according to the invention will be described with reference to FIGS. 1-12. The steps of a preferred embodiment of the method according to the invention are schematically illustrated in FIG. 14.

The method according to the invention is performed on a patient suffering from age-related macular degeneration (AMD) who has a pseudophakic eye, which means that at least one primary IOL 30 has already been implanted in the capsular bag 107 of the eye 100 in the posterior chamber 104. Both eyes of the patient may be pseudophakic and suffering from AMD, however, it is preferred to implant the secondary IOL 20 according to the invention into only one eye, preferably in the dominant (better-seeing) eye of the patient. The method according to the invention comprises introducing an IOL, such as the secondary IOL 20 according to any one of the previously described variants, between the pupil 105 of the eye 100 and the capsular bag 107 containing the at least one primary IOL 30; aligning the central optical lens portion of the secondary IOL 20 and fixing the secondary IOL 20 in the aligned position in the ciliary sulcus 102 via the haptics. According to the preferred embodiment illustrated in FIG. 14 this is carried out by performing the following steps.

In step S10 the pupil of the patient's eye which is to receive the secondary IOL 20 is dilated using any known techniques. In step S12 a small incision, preferably a micro-incision of about 2 to 2.5 mm is made on the cornea 112. After this, preferably an ophthalmic viscosurgical device (OVD) is introduced under the iris 106 in step S14. The OVD is a viscoelastic substance that serves to open up the potential space between the capsular bag 107 and the ciliary sulcus 102.

In step S16 the secondary IOL 20 is injected through the incision into the posterior chamber 104 between the iris 106 and the capsular bag 107. Prior to injection the secondary IOL 20, which is made of a foldable soft material, is preferably folded in a reverse U-shape, such that the haptics 2 are facing downward (posteriorly) in the direction of the ciliary sulcus 102. Folding and injecting can be carried out by known IOL delivery apparatuses comprising winglet-type cartridges. A second instrument can be used during the injection phase to go under the optically active lens part 1 in order to avoid downward pressure and thereby protect the primary IOL 30 already implanted in the capsular bag 107. After injection, at least the optically active lens part 1 of the IOL 20 unfolds in the space between the iris 106 and the capsular bag 107. Some or all of the haptics 2 may remain in a folded position facing downward, however. The central optical lens portion 1a of the optically active lens part 1 is aligned optically coaxial to the at least one primary IOL in step S18 for magnifying and focusing on the fovea 109 of the retina 108 an image projected through the primary IOL 30 by the central optical lens portion 1a when the secondary IOL 20 is used to view a near object. If the optically active lens part 1 is at least partially toric then aligning includes rotating the secondary IOL 20 into the intended position. The optically active lens part 1 preferably contains markings such as the projection 8a and recess 8b to help the alignment.

In step S20 the haptics 2 are arranged in the ciliary sulcus 102 by unfolding any haptics 2 that are still in a folded position and by tucking the haptics 2 under the iris 106. In this way the secondary IOL 20 is fixed in a stable manner in the aligned position.

In step S22 the OVD is removed through the incision after which any haptic 2 affected by the removal of the OVD may need to be rearranged in the ciliary sulcus 102 in step S24 for fixing the secondary IOL 20 firmly and stably.

The effect of the secondary IOL 20 can be understood by comparing FIGS. 12 and 13, which differ in the size of the pupil 105 formed by the iris 106.

FIGS. 12 and 13 illustrate the position of the secondary IOL 20 and the primary IOL 30 within a patient's eye 100. As can be seen, the secondary IOL 20 has been surgically implanted in the ciliary sulcus 102 of the pseudophakic eye 100, i.e. in addition to a primary IOL 30 that has already been implanted in the capsular bag 107 of the posterior chamber 104 of the patient's eye 100 prior to the implantation of the secondary IOL 20. The haptics 2 fix and stabilize the secondary IOL 20 within the ciliary sulcus 102 of the patient's eye 100. The optically active lens part 1 of the secondary IOL 20 is designed to project an image through the primary IOL 30 onto the retina 108 of the 100. The central optical lens portion 1a of the secondary IOL 20 is aligned optically coaxial to the primary IOL 30 for magnifying and focusing on the fovea 109 of the retina 109 an image of a near object, the image being magnified and projected through the primary IOL 30 by the central optical lens portion 1a of the secondary IOL 20 so as to obtain a magnified focused image as illustrated in FIG. 13.

In FIG. 12, the pupil 105 is constricted, thus light rays 120 entering the pupil 105 are restricted mainly to the central optical lens portion 1a of the secondary IOL 20 focusing a magnified image on the fovea 109 of the retina 108. This is the case when the patient focuses on nearby objects, i.e. reading a newspaper or a price tag, and the reflex of near vision miosis constricts the pupil 105.

The image of the near object, which is projected through the primary IOL 30 by the central optical lens portion 1a onto the fovea is magnified which enables the patient's eye 100 to resolve the image in case of AMD as well. Due to the relatively high refraction of the central optical lens portion 1a compared to the basic lens power, the sharp vision is at a near distance, d, for which the typical value is 5-20 cm.

In this way, the secondary IOL 20 improves the visual capabilities of the patient by additionally magnifying at least a central part of the image of the primary IOL 30 when the patient is viewing objects at near distance.

In FIG. 13, the eye 100 focuses on a distant object and the pupil 105 is dilated leaving enough space around the central optical lens portion 1a for light rays 120' to pass through the peripheral optical lens portion 1b of the secondary IOL 20 as well. The refractive power of the peripheral optical lens portion 1b can be chosen such that the light rays 120' coming from a distant object and propagating through the peripheral optical lens portion 1b will also be focused on the fovea 109 of the retina 108 by the primary IOL 30 thus forming the distant image, which will dominate in the patient's perception over the rays 120 passing through the central optical lens portion 1a that do not focus anywhere onto the retina 108 (dashed lines).

Various modifications to the above disclosed embodiments will be apparent to a person skilled in the art without departing from the scope of protection determined by the attached claims.

The invention claimed is:

1. A method for correction of near vision of a patient suffering from age-related macular degeneration (AMD) and having a pseudophakic eye having at least one primary intraocular lens (IOL) implanted in a capsular bag of the eye in a posterior chamber of the eye, comprising:

implanting a secondary IOL, made from a foldable soft material, between an iris of the eye and the capsular bag containing the at least one primary IOL, wherein the secondary IOL comprises an optically active lens part having an optical axis and a plurality of haptics evenly spaced about a periphery of the optically active lens part, the optically active lens part having a central optical lens portion and a peripheral optical lens portion surrounding the central optical lens portion, the central optical lens portion having a diameter smaller than 1.8 millimeters but bigger than 0.5 millimeters and being a positive lens having a refractive power that differs from a refractive power of the peripheral optical lens portion by +5 diopters up to +25 diopters, placing the central optical lens portion of the secondary IOL in an aligned position optically coaxial to the at least one primary IOL for magnifying and focusing an image projected by the central optical lens portion through the at least one primary IOL on a fovea of a retina of the eye, and fixing the secondary IOL in the aligned position by arranging the plurality of haptics adjacent the iris in a ciliary sulcus of the eye.

2. The method according to claim 1, comprising spacing the iris from the primary IOL by introducing an ophthalmic viscosurgical device under the iris prior to implanting the secondary IOL.

3. The method according to claim 1, wherein the peripheral optical lens portion is a lens with zero refraction.

4. The method according to claim 1, wherein the refractive power of the peripheral optical lens portion is between −5 diopters and +15 diopters.

5. The method according to claim 1, wherein the refractive power of the central optical lens portion differs from the refractive power of the peripheral optical lens portion by +8 diopters up to +12 diopters.

6. The method according to claim 1, wherein the optically active lens part has a diameter between 4 and 10 mm.

7. The method according to claim 1, wherein the central optical lens portion has a diameter smaller than 1.6 millimeters but bigger than 0.8 millimeters.

8. The method according to claim 1, wherein the ratio between a diameter of the central optical lens portion and the diameter of the optically active lens part is between 0.05 and 0.45.

9. The method according to claim 1, wherein the secondary intraocular lens is formed as a unitary single-piece intraocular lens.

10. The method according to claim 1, wherein the optically active lens part is at least partially toric.

11. The method according to claim 1, wherein the plurality of haptics of the optically active lens part has at least four haptics unitary with the optically active lens part, and said periphery of the optically active lens part has a non-convex rim between any two neighboring haptics of the at least four haptics, which non-convex rim is free from surface irregularities that interfere with the iris, each haptic of the at least four haptics comprising a closed loop, and a shoulder connecting the loop with the optically active lens part, the closed loops being elastically deformable in a plane perpendicular to the optical axis of the optically active lens part in a direction toward the optically active lens part.

12. The method according to claim 11, wherein each shoulder has a generally flat, triangular shape narrowing in the direction of the haptic loop connected therewith.

13. The method according to claim 11, wherein the shoulders have projections or recesses for performing a positioning function.

14. The method according to claim 11, wherein the optically active lens part comprises an angulated anterior face that angles anteriorly.

15. The method according to claim 11, wherein a posterior face of the optically active lens part is provided with spacing projections.

16. The method according to claim 11, wherein a posterior face of the optically active lens part has recesses that are centered on diameters passing through poles of two opposing loops.

17. The method according to claim 11, wherein in a state of maximum compression of the closed loops, the secondary IOL has an overall diameter between 10.5 mm and 12.5 mm.

18. The method according to claim 11, wherein each haptic loop comprises an elongated arched upper segment with opposed end portions and a pair of lower segments, each lower segment pivotably joined to the upper segment at one of said end portions of the upper segment and to the shoulder at a distance therebetween, such that said lower segments converge in the direction of the optically active lens part and a length of each upper segment is less than a sum of the lengths of said lower segments and said distance.

19. The method according to claim 18, wherein the lower segments of each loop lie at an angle not exceeding 100 degrees in an undeformed state of said loop and opening in a direction of the upper segment.

20. The method according to claim 18, wherein each lower segment is joined to the upper segment at one of said end portions of the upper segment at first flexion points, which are configured so as to make it possible for the arched upper segment and the two lower segments of each loop to pivot relative to each other about said first flexion points in said plane that is perpendicular to the optical axis of the optically active lens part, and each lower segment is joined to the shoulder at second flexion points, which are configured so as to make it possible for the two lower segments of each loop to pivot relative to the optically active lens part of the secondary IOL about said second flexion points in said plane that is perpendicular to the optical axis.

21. The method according to claim 18, wherein each lower segment is joined to the upper segment at one of said end portions of the upper segment at first flexion points and to the shoulder at second flexion points, the two lower segments and the upper segment of each loop are configured to occupy a non-deformed state in which the lower segments are lying at a first angle to each other and the first flexion points are at a first distance from each other, and an elastically deformed state in which the arched upper segment flattens, the lower segments are lying at a second angle to each other and the first flexion points are at a second distance from each other, the second angle being greater than the first angle and the second distance being greater than the first distance.

22. The method according to claim 18, wherein the arched upper segment in each closed loop is formed by at least two portions connected to each other by a third flexion point.

23. The method according to claim 18, wherein each lower segment is joined to the upper segment at one of said end portions of the upper segment at first flexion points and to the shoulder at second flexion points, and a cross-section of each loop at the first and the second flexion points of said loop is smaller than a cross-section of the lower segments and the upper segments.

24. The method according to claim 18, wherein an outer edge of the upper segment of each loop is ridged.

25. The method according to claim 18, wherein an outer edge of the lower segments of each loop is straight.

* * * * *